United States Patent [19]

Suzukamo et al.

[11] Patent Number: 4,727,204
[45] Date of Patent: * Feb. 23, 1988

[54] PROCESS FOR PREPARING 5-ETHYLIDENE-2-NORBORNENE WITH HIGH QUALITY

[75] Inventors: Gohfu Suzukamo, Osaka; Masami Fukao, Shiga; Fujio Masuko, Chiba; Masahiro Usui, Chiba; Kazuo Kimura, Chiba, all of Japan

[73] Assignee: Sumitomo Chemical Company, Limited, Osaka, Japan

[*] Notice: The portion of the term of this patent subsequent to Jan. 19, 2005 has been disclaimed.

[21] Appl. No.: 943,067

[22] Filed: Dec. 18, 1986

[30] Foreign Application Priority Data

Dec. 20, 1985 [JP] Japan .................. 60-288255
Dec. 27, 1985 [JP] Japan .................. 60-297274

[51] Int. Cl.$^4$ ............................ C07C 5/25
[52] U.S. Cl. .................. 585/377; 585/363
[58] Field of Search .................. 585/377, 363

[56] References Cited

U.S. PATENT DOCUMENTS 3,577,473  5/1971  Nagase et al. .................. 585/377
3,808,152  4/1974  Nagase et al. .................. 585/377
3,897,509  7/1975  Nagase et al. .................. 585/377

FOREIGN PATENT DOCUMENTS 769324  6/1971  Belgium .................. 585/377
0157222 10/1985  European Pat. Off. .
60-94925  5/1985  Japan .

Primary Examiner—Asok Pal
Attorney, Agent, or Firm—Birch, Stewart, Kolasch & Birch

[57] ABSTRACT

5-Ethylidene-2-norbornene with high quality is effectively prepared by isomerization 5-vinyl-2-norbornene containing 1 ppm to 0.5% by weight of 4-vinylcyclohexene in the presence of at least one catalyst selected from the group consisting of a solid base catalyst which is prepared by reacting alumina, an alkali metal hydroxide and an alkali metal in a temperature range of 200° to 500° C. and a solid base catalyst which is prepared by reacting water-containing alumina and an alkali metal in such an amount that exceeds a molar equivalent of water contained in alumina at a temperature in a range between a melting point of the alkali metal and 500° C. in an inert gas atmosphere.

18 Claims, No Drawings

PROCESS FOR PREPARING 5-ETHYLIDENE-2-NORBORNENE WITH HIGH QUALITY

BACKGROUND OF THE INVENTION

1. Field of the Invention

The present invention relates to a process for preparing 5-ethylidene-2-norbornene (hereinafter referred to as "ENB") with high quality. Particularly, the present invention relates to a process for preparing ENB by isomerizing 5-vinyl-2-norbornene (hereinafter referred to as "VNB") containing a certain amount of 4-vinylcyclohexene (hereinafter referred to as "VCH") in the presence of a specific solid base catalyst.

2. Background of the Invention

ENB is the most promising compound as a third monomer of a terpolymer of ethylene, propylene and dienemonomer (EDPM rubber) and prepared by isomerizing VNB in the presence of a catalyst. VNB is produced by reacting 1,3-butadiene and cyclopentadiene.

As the isomerization catalysts, there are known liquid bases such as mixtures of an alkali metal hydroxide and an aprotic organic solvent, of an alkali metal amide and an amine and of an organic alkali metal compound and an aliphatic amine. Such liquid bases, however, do not have enough catalytic activity so that a large amount of the expensive catalyst should be used. Further, since separation and recovering of the catalyst component from an reaction mixture are very difficult, the process requires complicated separation and recovering steps and consumes a large amount of energy.

There are also known solid isomerization catalysts, for example, an alkali metal carried on an anhydrous carrier with a large surface area (e.g., activated carbon, silica gel, alumina and the like) (cf. J. Am. Chem. Soc., 82, 387 (1960)). The solid catalyst, however, has unsatisfactory handleability and less safety because it is ignited and loses activity upon contact with air. This is because the alkali metal is only finely dispersed on the carrier. Further, the solid catalyst has insufficient isomerization performance.

The present inventors have proposed a solid base catalyst for isomerizing olefins such as VNB, which does not suffer from the drawbacks of the conventional isomerization catalysts. The proposed catalyst is prepared from alumina, an alkali metal hydroxide and an alkali metal, or from water-containing alumina and an alkali metal. The solid base catalyst has higher stability to air and excellent isomerization activity of olefins such as VNB than the alkali metal dispersion catalyst (cf. Japanese Patent Publication Nos. 35264/1974 and 29058/1980).

As a result of further study on the isomerization of VNB with the solid base catalyst, it was found that VNB with decreased quality was produced in some cases. When such VNB with decreased quality is used as a third monomer of EPDM, the of a polymerization catalyst is deteriorated and a molecular weight distribution is undesirably varied.

SUMMARY OF THE INVENTION

Accordingly, one object of the present invention is to provide a process for preparing ENB with high quality by isomerizing VNB containing VCH as an impurity in the presence of a solid base catalyst.

Another object of the present invention is to provide a process for preparing ENB which is so pure that it can be used in a subsequent process without any purification.

These and other objects are accomplished by a process for preparing ENB with high quality according to the present invention which comprises isomerizing VNB containing 1 ppm to 0.5% by weight of VCH in the presence of at least one solid base catalyst selected from a solid base catalyst which is prepared by reacting alumina, an alkali metal hydroxide and an alkali metal in a temperature range of 200° to 500° C. in an inert gas atmosphere and a solid base catalyst which is prepared by reacting water-containing alumina and an alkali metal in such an amount that exceeds a molar equivalent of water contained in alumina at a temperature in a range between a melting point of the alkali metal and 500° C. in an inert gas atmosphere.

DETAILED DESCRIPTION OF THE INVENTION

The process of the present invention has been completed based on the finding that, in the isomerization of VNB to ENB, a reason for decreasing the quality of ENB is VCH contained in VNB and that when the amount of the VCH in VNB is in a certain range, VNB is effectively converted to ENB having such high quality that it can be used as a third monomer of EPDM after removal of the catalyst without any further purification of ENB.

Examples of the alkali metal hydroxide are lithium hydroxide, sodium hydroxide, potassium hydroxide, rubidium hydroxide and cesium hydroxide and a mixture thereof. It may be used in a solid or liquid state.

As the alkali metal, an alkali metal of Group I of the Periodic Table such as sodium, potassium and rubidium is used. They may be used as a mixture or an alloy. Among them, sodium, potassium and an alloy thereof are preferred.

As a combination of the alkali metal and the alkali metal hydroxide, a combination of an alkali metal and a hydroxide of other alkali metal, for example a combination of potassium and sodium hydroxide, of sodium and potassium hydroxide or of sodium and lithium hydroxide can be used, although a combination of an alkali metal and its corresponding hydroxide, for example, a combination of sodium and sodium hydroxide, of potassium and potassium hydroxide, and the like may be usually used. A combination of metal sodium and sodium hydroxide is preferably used in technology. Amounts of the alkali metal and the alkali metal hydroxide are 2 to 10% by weight and 5 to 40% by weight, respectively based on the weight of alumina in view of the catalytic activity.

Usually, alumina with a relatively large surface area such as γ-, χ-, ρ- and η-alumina is used. Among them, alumina of 50 to 500 mesh, particularly, γ-alumina of such mesh is preferred in view of the catalytic activity. Since alumina acts as a carrier in addition it reacts with the alkali metal and the alkali metal hydroxide, an alumina-containing compound such as kaolin and alumina silicate may be used in place of alumina.

According to the present invention, alumina, the alkali metal and the alkali metal hydroxide are reacted at a specific temperature as described above to prepare the solid base catalyst. As to the sequence of the reactions, preferably, alumina and the alkali metal hydroxide are firstly reacted and then the alkali metal is reacted. Usually, the alkali metal hydroxide kept at a temperature higher than its melting point is added to alumina and reacted at the specific temperature, although an aqueous solution of the alkali metal hydroxide may be used and the reaction mixture is heated to the specific temperature to promote the reaction. Also, the alkali metal is added at a temperature higher than its melting point and reacted at the specific temperature, although it can be added in the form of a solution and heated to the specific temperature to promote the reaction. The reactions are preferably carried out in an atmosphere of an inert gas such as nitrogen, helium and argon.

In the preparation of the catalyst, the reaction temperature is important since it has a great influence on the properties of the prepared solid base catalyst. Usually, the temperature is from 200° to 500° C. Preferably, alumina and the alkali metal hydroxide are reacted in a temperature range of 250° to 450° C. Preferably, the alkali metal is reacted in a temperature range of 200° to 330° C. When the catalyst is prepared in the above temperature range, it has considerably high activity so that the objective reaction can proceed in the presence of a small of amount of the catalyst.

The reaction time varies with other reaction conditions such as temperature. The reaction of alumina and the alkali metal hydroxide may be completed within 0.5 to 10 hours, and that of the alkali metal may be completed within 10 to 300 minutes.

In addition to the above method, the solid base catalyst to be used in the process of the present invention can be prepared by reacting water-containing alumina and the alkali metal. This may be due to the formation of the alkali metal hydroxide from water contained in alumina and the alkali metal. Such preparation of the catalyst will be illustrated hereinafter.

Various types of water-containing alumina except α-alumina can be used.

Generally, alumina is produced by calcining aluminum hydroxide. According to the calcining temperature and time, alumina has various metastable states and a water content varies so that various kinds of alumina are produced. In the present invention, such alumina may be used. Preferably, the water-containing alumina with a large surface area such as γ-, χ-, ρ- and η-alumina is used.

Although it is rather difficult to measure the water content of alumina, water content may be expressed by weight loss on heating in the heating step in which alumina in its original state is changed to α-alumina which is considered to include no removable water. Usually, the water content of water-containing alumina is 1.3 to 10% by weight, preferably 2 to 7% by weight in terms of weight loss on heating.

The alkali metal used in this preparation is the same as described above. A total amount of the alkali metal to be reacted is larger than such amount that corresponds to a molar equivalent of water contained in alumina, preferably 1.01 to 2 time molar equivalents of water contained in alumina.

According to the present invention, water-containing alumina is reacted with the alkali metal in at least such an amount that corresponds to the molar equivalent of water contained in alumina preferably in an atmosphere of an inert gas such as nitrogen, helium and argon, and then excess amount of alkali metal is reacted with alumina. In this method, of kind of the alkali metal firstly reacted and that of the alkali metal subsequently reacted may be the same or different.

Also in this second preparation of the solid base catalyst, the reaction temperatures is important and usually varies from the melting point of the alkali metal to 500° C. The reaction temperature in the second step has significant influence on the properties of the catalyst.

In the first reaction of water-containing alumina and the alkali metal in an amount corresponding to the molar equivalent of contained water, a reaction temperature is in a range between a melting point of the alkali metal and 500° C. In the second reaction of alumina and excess alkali metal, a reaction temperature is 180° to 350° C., preferably 200° to 330° C. When the catalyst is prepared in the above temperature range, it has considerably high activity so that the objective reaction can proceed in the presence of a small of amount of the catalyst. Preferably, the first reaction temperature and the second reaction temperature are substantially the same. In such case, the reaction temperature is preferably from 180° to 350° C., more preferably from 200° to 330° C. In this case, the alkali metal can be added in one portion.

The reaction time varies with other reaction conditions such as the reaction temperature. Usually, it is 15 minutes to 10 hours.

In the process of the invention, VNB is isomerized to ENB in the presence of the solid base catalyst as prepared above. VNB to be isomerized by the process of the present invention contains 1 ppm to 0.5% by weight of VCH, preferably 5 ppm to 0.1% by weight. Such VNB may be obtained by distillating a reaction product of butadiene and cyclopentadiene.

When VNB contains more than 0.5% by weight of VCH, the quality of produced ENB is unsatisfactory so that it cannot be used as the third monomer of EPDM only after removal of the catalyst. Therefore, such ENB should be purified by complicated troublesome rectification. To produce ENB with high quality, it is essential to isomerize VNB containing the reduced amount of VCH.

A weight ratio of the catalyst to VNB is 1:2,000 to 1:5, preferably 1:1,000 to 1:20.

Since the isomerization proceeds at an ordinary temperature, it is not necessary to heat the reaction system. To accelerate the isomerization, the reaction temperature may be elevated. Usually, the reaction temperature is in a range between −30° to +120° C., preferably between −10° to +100° C.

The isomerization is effected without any reaction medium, although it may be carried out in an inert liquid medium such as a hydrocarbon (e.g., pentane, hexane, heptane and dodecane).

The isomerization of the present invention may be carried out batch wise or continuously. The isomerization is preferably carried in an atmosphere of an inert gas. If necessary, VNB is pretreated with a desiccant such as alumina prior to isomerization.

The isomerization product is analyzed by a known method such as gas chromatography and separated from the catalyst by a conventional separation method such as filtration.

ENB prepared according to the present invention is very pure without purification and can be used as the third monomer of EPDM and the like.

Practically and presently preferred embodiments of the present invention will be illustrated by following examples.

REFERENCE EXAMPLE 1

To a 100 ml flask, γ-alumina (31.9 g) was added and heated under nitrogen with stirring at a temperature of 490°–500° C. for one hour. After cooling to 310°–320° C., sodium hydroxide (3.0 g) was added thereto and stirred at the same temperature for 3 hours.

Then, metal sodium (1.5 g) was added, stirred at the same temperature for one hour and then cooled to room temperature to obtain a solid catalyst (33.9 g).

REFERENCE EXAMPLE 2

To a 100 ml flask, γ-alumina (31.9 g) was added and heated under nitrogen with stirring at a temperature of 490°–500° C. for one hour. After cooling to 310°–320° C., sodium hydroxide (3.0 g) was added thereto and stirred at the same temperature for 3 hours.

After cooling down to 270°–280° C., metal sodium (1.5 g) was added, stirred at the same temperature for one hour and then cooled to room temperature to obtain a solid catalyst (33.7 g).

REFERENCE EXAMPLE 3

To a 100 ml flask, γ-alumina (50.0 g) was added and heated under nitrogen with stirring at a temperature of 490°–500° C. for 30 minutes. After cooling to 390°–400° C., sodium hydroxide (7.5 g) was added thereto and stirred at the same temperature for 1.5 hours.

Then, metal sodium (2.0 g) was added, stirred at the same temperature for two hours and then cooled to room temperature to obtain a solid catalyst (56.5 g).

REFERENCE EXAMPLE 4

To a 100 ml flask, γ-alumina containing 2.0% by weight of water (30.0 g) was added and heated under nitrogen with stirring at a temperature of 290°–300° C. Then, metal sodium (0.9 g) was added, stirred at the same temperature for one hour and then cooled to room temperature to obtain a solid catalyst (30.7 g).

REFERENCE EXAMPLE 5

To a 100 ml flask, γ-alumina containing 2.2% by weight of water (30.0 g) was added and heated under nitrogen with stirring at a temperature of 310°–320° C. Then, metal sodium (1.2 g) was added, stirred at the same temperature for one hour and then cooled to room temperature to obtain a solid catalyst (30.7 g).

REFERENCE EXAMPLE 6

To a 100 ml flask, γ-alumina containing 2.2% by weight of water (30.0 g) was added and heated under nitrogen with stirring at a temperature of 400°–410° C. for one hour. Then, metal sodium (1.2 g) was added, stirred at the same temperature for one hour and then cooled to room temperature to obtain a solid catalyst (30.6 g).

EXAMPLE 1

To a 100 ml flask containing the catalyst prepared in Reference Example 1 (0.18 g), VNB (purity, 99.9%. 45.0 g) containing 20 ppm of VCH was added under nitrogen and stirred at 20° C. for 5 hours.

Thereafter, the solid catalyst was filtered off to obtain a reaction mixture (44.6 g. Yield 99%). Gas chromatographic analysis of the mixture revealed that following compounds were contained in the mixture:

| Compound | % by mole |
| --- | --- |
| VCH | (Not detected) |
| Ethylbenzene | 0.002 |
| VNB | 0.25 |
| ENB | 99.62 |
| 2-Ethylidene norbornane | 0.002 |
| 1-Vinyl-nortricyclene | 0.02 |

EXAMPLE 2

To a 100 ml flask containing the catalyst prepared in Reference Example 2 (0.19 g), VNB (purity, 99.9%. 48.5 g) containing 20 ppm of VCH was added under nitrogen and stirred at 15° C. for 6 hours.

Thereafter, the solid catalyst was filtered off to obtain a reaction mixture (47.9 g. Yield 99%). Gas chromatographic analysis of the mixture revealed that following compounds were contained in the mixture:

| Compound | % by mole |
| --- | --- |
| VCH | (Not detected) |
| Ethylbenzene | 0.002 |
| VNB | 0.36 |
| ENB | 99.51 |
| 2-Ethylidene norbornane | 0.002 |
| 1-Vinyl-nortricyclene | 0.02 |

EXAMPLE 3

To a 100 ml flask containing the catalyst prepared in Reference Example 1 (0.17 g), VNB (purity, 99.8%. 42.5 g) containing 0.1% by weight of VCH was added under nitrogen and stirred at 50° C. for 5 hours.

Thereafter, the solid catalyst was filtered off to obtain a reaction mixture (41.7 g. Yield 98%). Gas chromatographic analysis of the mixture revealed that following compounds were contained in the mixture:

| Compound | % by mole |
| --- | --- |
| VCH | (Not detected) |
| Ethylbenzene | 0.10 |
| VNB | 0.30 |
| ENB | 99.28 |
| 2-Ethylidene norbornane | 0.08 |
| 1-Vinyl-nortricyclene | 0.03 |

EXAMPLE 4

To a 100 ml flask containing the catalyst prepared in Reference Example 3 (0.36 g), VNB (purity, 99.9%. 42.0 g) containing 20 ppm of VCH was added under nitrogen and stirred at 20° C. for 5 hours.

Thereafter, the solid catalyst was filtered off to obtain a reaction mixture (41.3 g. Yield 98%). Gas chromatographic analysis of the mixture revealed that following compounds were contained in the mixture:

| Compound | % by mole |
| --- | --- |
| VCH | (Not detected) |
| Ethylbenzene | 0.002 |
| VNB | 0.32 |
| ENB | 99.47 |
| 2-Ethylidene norbornane | 0.002 |
| 1-Vinyl-nortricyclene | 0.04 |

EXAMPLE 5

To a 100 ml flask containing the catalyst prepared in Reference Example 1 (0.21 g), VNB (purity, 99.5%. 31.5 g) containing 0.4% by weight of VCH was added under nitrogen and stirred at 30° C. for 5 hours.

Thereafter, the solid catalyst was filtered off to obtain a reaction mixture (31.0 g. Yield 98%). Gas chromatographic analysis of the mixture revealed that following compounds were contained in the mixture:

| Compound | % by mole |
| --- | --- |
| VCH | (Not detected) |
| Ethylbenzene | 0.38 |
| VNB | 0.32 |
| ENB | 98.77 |
| 2-Ethylidene norbornane | 0.36 |
| 1-Vinyl-nortricyclene | 0.02 |

COMPARATIVE EXAMPLE 1

To a 100 ml flask containing the catalyst prepared in Reference Example 3 (0.30 g), VNB (purity, 98.6%. 30.0 g) containing 1.3% by weight of VCH was added under nitrogen and stirred at 20° C. for 8 hours.

Thereafter, the solid catalyst was filtered off to obtain a reaction mixture (29.6 g. Yield 99%). Gas chromatographic analysis of the mixture revealed that following compounds were contained in the mixture:

| Compound | % by mole |
| --- | --- |
| VCH | (Not detected) |
| Ethylbenzene | 1.3 |
| VNB | 0.33 |
| ENB | 96.92 |
| 2-Ethylidene norbornane | 1.21 |
| 1-Vinyl-nortricyclene | 0.07 |

EXAMPLE 6

To a 100 ml flask containing the catalyst prepared in Reference Example 4 (0.18 g), VNB (purity, 99.9%. 37.7 g) containing 20 ppm of VCH was added under nitrogen and stirred at 20° C. for 8 hours.

Thereafter, the solid catalyst was filtered off to obtain a reaction mixture (37.0 g. Yield 98%). Gas chromatographic analysis of the mixture revealed that following compounds were contained in the mixture:

| Compound | % by mole |
| --- | --- |
| VCH | (Not detected) |
| Ethylbenzene | 0.002 |
| VNB | 0.39 |
| ENB | 99.47 |
| 2-Ethylidene norbornane | 0.002 |
| 1-Vinyl-nortricyclene | 0.03 |

EXAMPLE 7

To a 100 ml flask containing the catalyst prepared in Reference Example 5 (0.24 g), VNB (purity, 99.5%. 59.0 g) containing 0.4% by weight of VCH was added under nitrogen and stirred at 15° C. for 8 hours.

Thereafter, the solid catalyst was filtered off to obtain a reaction mixture (58.3 g. Yield 99%). Gas chromatographic analysis of the mixture revealed that following compounds were contained in the mixture:

| Compound | % by mole |
| --- | --- |
| VCH | (Not detected) |
| Ethylbenzene | 0.39 |
| VNB | 0.49 |
| ENB | 98.59 |
| 2-Ethylidene norbornane | 0.32 |
| 1-Vinyl-nortricyclene | 0.03 |

EXAMPLE 8

To a 100 ml flask containing the catalyst prepared in Reference Example 4 (0.20 g), VNB (purity, 99.9%. 40.6 g) containing 20 ppm of VCH was added under nitrogen and stirred at 50° C. for 5 hours.

Thereafter, the solid catalyst was filtered off to obtain a reaction mixture (39.8 g. Yield 98%). Gas chromatographic analysis of the mixture revealed that following compounds were contained in the mixture:

| Compound | % by mole |
| --- | --- |
| VCH | (Not detected) |
| Ethylbenzene | 0.002 |
| VNB | 0.35 |
| ENB | 99.48 |
| 2-Ethylidene norbornane | 0.002 |
| 1-Vinyl-nortricyclene | 0.004 |

EXAMPLE 9

To a 100 ml flask containing the catalyst prepared in Reference Example 6 (0.52 g), VNB (purity, 99.9%. 63.3 g) containing 20 ppm of VCH was added under nitrogen and stirred at 20° C. for 8 hours.

Thereafter, the solid catalyst was filtered off to obtain a reaction mixture (62.6 g. Yield 99%). Gas chromatographic analysis of the mixture revealed that following compounds were contained in the mixture:

| Compound | % by mole |
| --- | --- |
| VCH | (Not detected) |
| Ethylbenzene | 0.002 |
| VNB | 0.28 |
| ENB | 99.56 |
| 2-Ethylidene norbornane | 0.002 |
| 1-Vinyl-nortricyclene | 0.03 |

COMPARATIVE EXAMPLE 2

To a 100 ml flask containing the catalyst prepared in Reference Example 4 (0.25 g), VNB (purity, 98.6%. 46.9 g) containing 1.3% by weight of VCH was added under nitrogen and stirred at 20° C. for 8 hours.

Thereafter, the solid catalyst was filtered off to obtain a reaction mixture (46.3 g. Yield 99%). Gas chromatographic analysis of the mixture revealed that following compounds were contained in the mixture:

| Compound | % by mole |
| --- | --- |
| VCH | (Not detected) |
| Ethylbenzene | 1.24 |
| VNB | 0.32 |
| ENB | 96.91 |
| 2-Ethylidene norbornane | 1.20 |
| 1-Vinyl-nortricyclene | 0.03 |

What is claimed is:

1. A process for preparing 5-ethylidene-2-norbornene with high quality which comprises isomerizing 5-vinyl-2-norbornene containing 1 ppm to 0.5% by weight of 4-vinylcyclohexene in the presence of at least one solid base catalyst selected from the group consisting of a solid base catalyst which is prepared by reacting alumina, an alkali metal hydroxide and an alkali metal in a temperature range of 200° to 500° C. in an inert gas atmosphere and a solid base catalyst which is prepared by reacting water-containing alumina and an alkali metal in such an amount that exceeds a molar equivalent of water contained in alumina at a temperature in a range between a melting point of the alkali metal and 500° C. in an inert gas atmosphere.

2. The process according to claim 1, wherein the solid base catalyst is one prepared by heating alumina, an alkali metal hydroxide and an alkali metal.

3. The process according to claim 2, wherein alumina and the alkali metal hydroxide are reacted in a temperature range of 250° to 450° C.

4. The process according to claim 2, wherein the alkali metal is reacted in a temperature range of 200° to 330° C.

5. The process according to claim 2, wherein the alkali metal hydroxide is selected from the group consisting of lithium hydroxide, sodium hydroxide, potassium hydroxide and cesium hydroxide and mixtures thereof.

6. The process according to claim 2, wherein alumina is selected from the group consisting of γ-alumina, χ-alumina, ρ-alumina, η-alumina and mixtures thereof.

7. The process according to claim 6, wherein alumina is γ-alumina of 50 to 500 mesh.

8. The process according to claim 1, wherein the solid base catalyst is prepared by heating water-containing alumina and an alkali metal.

9. The process according to claim 8, wherein the alkali metal is used in such an amount that corresponds to 1.01 to 2 time molar equivalents of water contained in alumina.

10. The process according to claim 8, wherein the water-containing alumina and the excess portion of the alkali metal to the molar equivalent of water contained in alumina are reacted at a temperature of 200° to 330° C. in the preparation of the catalyst.

11. The process according to claim 8, wherein alumina and the molar equivalent amount of the alkali metal, and alumina and the excess molar equivalent amount of the alkali metal are reacted at a temperature of 200° to 330° C. in the preparation of the catalyst.

12. The process according to claim 8, wherein water-containing alumina is selected from the group consisting of γ-alumina, χ-alumina and ρ-alumina which are preferably prepared by calcination of aluminum hydroxide.

13. The process according to claim 8, wherein the water content of alumina is 1.3 to 10% by weight.

14. The process according to claim 8, wherein the water content of alumina is 2 to 7% by weight.

15. The process according to claim 2, wherein the alkali metal is at least one selected from the group consisting of sodium, potassium and rubidium and mixtures and alloys thereof.

16. The process according to claim 8, wherein the alkali metal is at least one selected from the group consisting of sodium, potassium and rubidium and mixtures and alloys thereof.

17. The process according to claim 1, wherein the content of 4-vinylcyclohexene is from 5 ppm to 0.1% by weight.

18. The process according to claim 1, wherein the isomerization temperature range is from −10° to +100° C.

* * * * *